United States Patent [19]

Scheepens et al.

[11] Patent Number: 4,628,036
[45] Date of Patent: Dec. 9, 1986

[54] IMMUNOLOGICAL ASSAY WITH TEST TUBE HAVING BOTTOM FORMING A STRIP

[75] Inventors: Antonius H. J. M. Scheepens, Vlijmen; Hans van Hell, Oss; Hendrikus J. J. Theunissen, Ravenstein, all of Netherlands

[73] Assignee: Akzo N.V., Arnhem, Netherlands

[21] Appl. No.: 518,801

[22] PCT Filed: Nov. 24, 1982

[86] PCT No.: PCT/NL82/00043
§ 371 Date: Jun. 21, 1983
§ 102(e) Date: Jun. 21, 1983

[87] PCT Pub. No.: WO83/02009
PCT Pub. Date: Jun. 9, 1983

[30] Foreign Application Priority Data

Nov. 26, 1981 [NL] Netherlands .......................... 8105341

[51] Int. Cl.⁴ ............................................ G01N 33/555
[52] U.S. Cl. ..................... 436/520; 422/102; 436/805; 436/808; 436/810; 436/818
[58] Field of Search ............... 436/805, 520, 808, 810, 436/818; 422/72, 102

[56] References Cited

U.S. PATENT DOCUMENTS

| | | | |
|---|---|---|---|
| 4,148,607 | 4/1979 | Bernoco | 422/72 |
| 4,290,997 | 9/1981 | Suovaniemi | 436/805 X |
| 4,297,104 | 10/1981 | Matte | 422/72 X |
| 4,303,616 | 12/1981 | Kano | 422/102 |
| 4,427,634 | 1/1984 | Truglio | 422/102 |
| 4,466,740 | 8/1984 | Kano | 422/102 X |

FOREIGN PATENT DOCUMENTS 3022940 4/1981 Fed. Rep. of Germany .
2213711 8/1974 France .

OTHER PUBLICATIONS

Patent Abstracts of Japan, vol. 4, No. 95, Jul. 9, 1980, p. 19P18.

*Primary Examiner*—Sidney Marantz
*Attorney, Agent, or Firm*—Abelman Frayne Rezac & Schwab

[57] ABSTRACT

The present invention relates to the carrying out of immunochemical reactions in a test tube having a bottom in the shape of an inverted prism or truncated prism, in such a way that the lower edge of the tube forms a strip having a length which is at least equal to one-quarter of the distance between two opposite walls, or where appropriate to a quarter of the diameter of the test tube, as a result of which both the sensitivity and the readability are improved.

7 Claims, 4 Drawing Figures

IMMUNOLOGICAL ASSAY WITH TEST TUBE HAVING BOTTOM FORMING A STRIP

DIAGNOSTIC TEST METHOD

The invention relates to a method for qualitatively or semi-quantitatively detecting the presence of an antigen or antibody in a test liquid, and also to a test kit which permits carrying out such a method.

The diagnosis of pathological conditions in man or animals is frequency carried out by using immunochemical reactions. In general, the presence of an antigen or antibody in a body fluid is determined immunologically by bringing into contact with corresponding antibody or antigen with the particular body fluid to be tested, usually blood serum or urine.

The presence of the antigen or antibody to be detected can then be noted by the fact that a less soluble antigen-antibody complex is formed.

Such complexes are formed rather slowly and only at relatively high concentrations of antigen and antibody. It is therefor necessary, in order to increase the sensitivity, to use carriers in order to permit the detection of this type of complex and hence also of the particular antigens and antibodies.

The coupling of antigens and antibodies to a carrier is a known technique which is described in all immunological handbooks. Extensively used carrier are, inter alia: erythrocytes, cacterial cells, bentonite, latex particles and cellulose. In the present diagnostic test met hod, use is made of erythrocytes as carriers.

The presence of, for example, an antigen in a test sample or test liquid can now be demonstrated by bringing the test sample into contact with antibodies against this antigen, which are coupled to erythrocytes. If the antigen actually is present in the test sample, an immunochemical reaction will take place between the particular antigen and the antibody which is coupled to erythrocytes, resulting in an antigen-antibody complex coupled to erythrocytes and in a coupling together (agglutination) of such erythrocyte particles; on settling out in a test tube having a round bottom, these agglutinated erythrocytes give a plain light brown pattern.

If the antigen is not present in the test liquid, no immunochemical reaction, hence also no agglutination, can take place. The antibody bonded to erythrocytes will settle out after a short time and give a characteristic ring pattern in a test tube having a round bottom.

In this test set-up, obtaining a characteristic ring pattern in the test tube therefore means that the suspected antigen is not present in the test liquid, and therefore that the test result is negative.

The antigen in question can also be detected in a different manner, namely by bringing the test sample into contact with 2 reagents:

(1) the antibody against the particular antigen and
(2) the particular antigen coupled to erythrocytes.

If the antigen in question is *not* present in the test liquid, an immunological reaction will take place between the two added reagents, resulting in an agglutination of an erythrocyte-bonded antigen-antibody complex, which on settling out will not give a characteristic ring pattern.

If the antigen in question *is* present in the test liquid, this antigen will react directly with the antibody, giving a (soluble) antigen-antibody complex, while the unused erythrocyte-coupled antigen will settle out after a short time and, in a test tube with a round bottom, lead to the formation of a characteristic ring pattern.

In this test set-up, obtaining a characteristic ring pattern therefore means that the test result is positive.

Though the interpretation of the test result therefore depends on the chosen test set-up, the characteristic ring pattern of the erythrocyte-bonded antigen or antibody each time forms the basis of the test method.

Hitherto, the tests outlined above have been carried out in conventional round-bottomed test tubes. In such test tubes, the characteristic ring pattern of non-agglutinated erythrocytes manifests itself as a more or less thick ring.

Surprisingly, it has now been found that carrying out these immunochemical reactions in a test tube having a bottom in the shape of an inverted prism or truncated prism, such that the lower edge of the tube forms a strip having a length which is at least equal to one-fourth of the distance between two opposite walls or where appropriate to a quarter of the diameter of the test tube, (a) assists the readability of the test result, so that significantly fewer incorrect observations are made and
(b) increase the sensitivity of the test by a factor of 2 to 3; this means that the antigen or antibody can now be detected in lower concentrations than is possible with a conventional round-bottomed test tube.

The use of the test tube according to the invention can moreover have the optical advantage that the immunological test can be set up in such a way that a negative result manifests itself as a characteristic precipitate in the form of a minus-sign.

The test tubes which are used within the scope of the present invention are made of a transparent material, for example of glass or of a transparent plastic. The shape of these test tubes, other than the shape of the bottom, is immaterial; the tubes can therefore be of square, rectangular, circular or oval cross-section.

Figure 1:
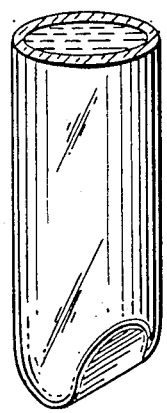
FIG. 1 is a perspective view of the lower portion of a test tube of the present invention.
Figure 2:
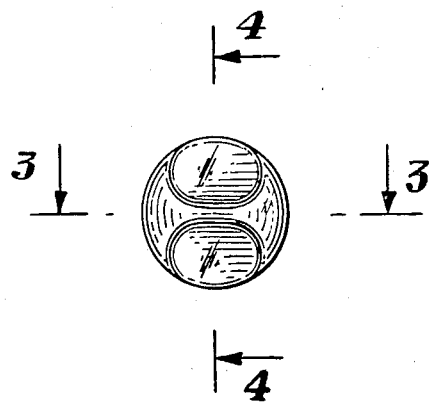
FIG. 2 is a bottom view thereof.
Figure 3:
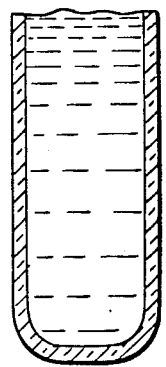
FIG. 3 is a sectional view through 3—3 of FIG. 2.
Figure 4:
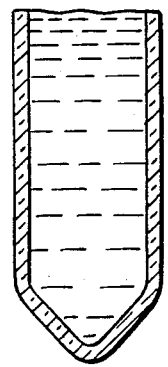
FIG. 4 is a sectional view through 4—4 of FIG. 4.

As already mentioned, the bottom of the test tubes must have the shape of an inverted prism or truncated prism, as a result of which the lower edge of the tube narrows to, as it were, a strip. The walls of the prism can moreover be bent slightly outwards.

The characteristic precipitate formed in an immunochemical determination, and which, depending on the chosen test set-up, can indicate a positive result or a negative result, now forms in the strip-shaped end of the test tube. It must be assumed that the precipitate in the shape of a minus-sign provides a more characteristic sedimentation pattern—especially for laymen who do not carry out such tests very frequently—than the pattern obtained in the round-bottomed tubes, thus explaining the better readability of the test.

The preferred test tubes according to the invention are cylindrical, with a diameter of, preferably, between 0.5 and 1.5 cm, and a bottom in the shape of an inverted truncated prism, the lower edge of the bottom forming a strip having a length which is at least equal to a quarter of the diameter of the test tube and preferably having a length equal to 50–85% of the diameter of the test tube.

The depth of the inverted prism (or truncated prism) is not particularly critical; however a preferred "depth" is approximately equal to 25–75% of the diameter of the test tube and more especially 40–50% of the diameter of the test tube.

The test method according to the invention can be employed for various types of diagnostic test purposes, for example for the qualitative detection of pathological antibodies in blood or urine, but also for the detection of HCG in urine, as a result of which the test method is particularly suitable as a pregnancy test.

We claim:

1. Method for qualitatively or semi-quantitavely detecting the presence of an antigen or antibody in a test liquid by bringing this test liquid into contact either with an erythrocyte-coupled binding partner of the antigen or antibody to be detected, or with a mixture of an erythrocyte-coupled antigen or erythrocyte-coupled antibody itself and the binding partner of the antigen or antibody to be detected, which is not coupled to a carrier, and thereafter ascertaining the presence or absence of the antigen or antibody in the test liquid from the characteristic sedimentation pattern of the erythrocytes formed at the bottom of a test tube, comprising carrying out the test in a test tube having a bottom in the shape of an inverted prism or trucated prism such that the lower edge of the test tube forms a strip having a length which is at least equal to one-fourth of the distance between two opposite walls of the test tube or at least equal to one-fourth of the diameter of the test tube and wherein the sedimentation pattern is read as formed at the bottom of the test tube.

2. Method according to claim 1 for detecting the presence or absence of the protein HCG in urine, by bringing a urine sample into contact, in the test tube, with an erythrocyte-coupled anti-HCG and, after 1 to 2 hours, detecting a characteristic sedimentaiton pattern, in the form of a minus-sign, if HCG is absent in the urine sample.

3. Method according to claim 1, wherein the bottom of the test tube has the shape of an inverted truncated prism having a depth of 25–75%, of the diameter, or the distance between 2 opposite walls of the test tube.

4. The method of claim 3 wherein the prism depth is 40–50% of the test tube diameter.

5. Test kit for carrying out the process as defined in claim 1, which kit comprises at least the following:
   (a) a test tube having a bottom in the shape of an inverted prism or truncated prism, such that the lower edge of the test tube forms a strip or line having a length which is at least equal to one-fourth of the distance between 2 opposite walls of the test tube or at least equal to one-fourth of the diameter of the test tube, and
   (b) the immunological reagents required for carrying out the immunological determination.

6. Test kit according to claim 5 comprising:
   (a) a test tube having a bottom in the shape of an inverted prism or truncated prism, having a depth of 25–75% and of the diameter or the distance between opposite walls of the test tube such that the lower edge of the test tube forms a strip or line having a length which is at least equal to one-fourth of the distance between 2 opposite walls or at least equal to one-fourth of the diameter of the test tube, and
   (b) the immunological reagents required for carrying out the immunological determination.

7. The kit of claim 6 wherein the prism depth is 40–50% of the test tube diameter.

* * * * *